US00PP34890P2

(12) United States Plant Patent
Janes et al.

(10) Patent No.: US PP34,890 P2
(45) Date of Patent: Jan. 3, 2023

(54) ***VERONICA* PLANT NAMED 'BALSKYWINK'**

(50) Latin Name: ***Veronica* hybrid**
Varietal Denomination: 'Balskywink'

(71) Applicant: Ball Horticultural Company, West Chicago, IL (US)

(72) Inventors: Jessica Diane Janes, Elkton, MD (US); Emily E. Alff, Royersford, PA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/948,777

(22) Filed: Sep. 20, 2022

(51) Int. Cl.
*A01H 5/02* (2018.01)
*A01H 6/68* (2018.01)

(52) U.S. Cl.
USPC ..... Plt./251
CPC ..... *A01H 6/68* (2018.05)

(58) Field of Classification Search
USPC ..... Plt./251
CPC ..... A01H 6/68; A01H 5/02
See application file for complete search history.

*Primary Examiner* — Keith O. Robinson
(74) *Attorney, Agent, or Firm* — Audrey Charles

(57) ABSTRACT

A new and distinct cultivar of *Veronica* plant named 'Balskywink', characterized by its medium reddish-purple colored flowers, dark green-colored foliage, and moderately vigorous, compact, upright growth habit, is disclosed.

1 Drawing Sheet

Latin name of genus and species of plant claimed: *Veronica* hybrid.

Variety denomination: 'Balskywink'.

BACKGROUND OF THE INVENTION

The present invention relates to a new and distinct cultivar of *Veronica* plant botanically known as *Veronica* hybrid and hereinafter referred to by the cultivar name 'Balskywink'.

The new cultivar originated in a controlled breeding program in Cochranville, Pa., during November 2016. The objective of the breeding program was the development of *Veronica* cultivars that have attractive colored inflorescences, strong stems and a compact, upright growth habit.

The new *Veronica* cultivar was the result of cross-pollination. The female (seed) parent of the proprietary *Veronica spicata* breeding selection coded X14-6480-4, not patented, characterized by its medium pink-colored flowers, dark green-colored foliage, and moderately vigorous, compact growth habit. The male (pollen) parent of the new cultivar is First Love 'Allove', U.S. Plant Pat. No. 21,478, characterized by its intense red-purple colored flowers, medium green-colored foliage, and moderately vigorous upright, inverted triangle growth habit. The new cultivar was discovered and selected as a single flowering plant within the progeny of the above stated cross-pollination during September 2017 in a controlled environment in Cochranville, Pa.

Asexual reproduction of the new cultivar by terminal stem cuttings since September 2017 in Cochranville, Pa. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balskywink' as a new and distinct cultivar of *Veronica* plant:

1. Medium reddish-purple colored flowers;
2. Dark green-colored foliage; and
3. Moderately vigorous, compact, upright growth habit.

Plants of the new cultivar differ from plants of the female parent primarily in having longer inflorescences and a more upright growth habit. Plants of the new cultivar differ from plants of the male parent primarily in having darker green-colored foliage and a lighter reddish-purple flower color.

Of the many commercially available *Veronica* cultivars, the most similar in comparison to the new cultivar is MOODY BLUES Pink 'Novaverpin', U.S. Plant Pat. No. 25,748. However, in side-by-side comparisons, plants of the new cultivar differ from plants of 'Novaverpin' in at least the following characteristics:

1. Plants of the new cultivar have shorter racemes than plants of 'Novaverpin';
2. Plants of the new cultivar have darker reddish-purple colored flowers than plants of 'Novaverpin'; and
3. Plants of the new cultivar have fewer flowers per inflorescence than plants of 'Novaverpin'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balskywink'. The plants were approximately four months old and grown three plants per pot in one-gallon containers for approximately two months in an outdoor nursery environment in West Chicago, Ill. Plants were given one pinch at approximately two weeks before transplant and another one week after transplant.

DETAILED BOTANICAL DESCRIPTION

Figure 1:
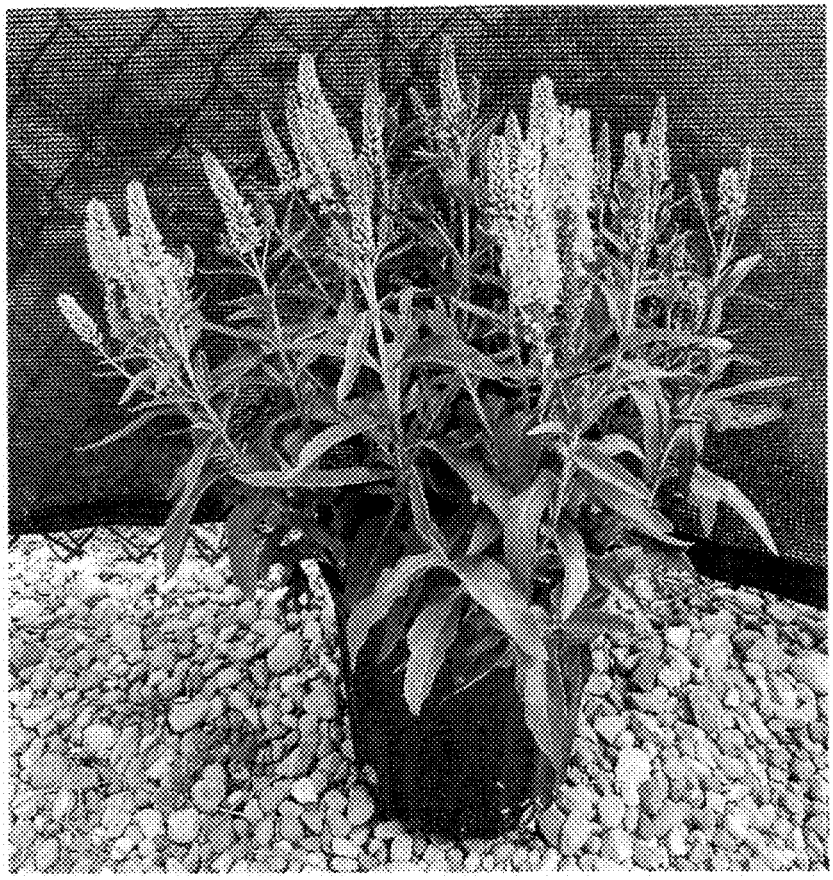
FIG. 1 illustrates a side view of the overall growth and flowering habit of 'Balskywink'.
Figure 2:
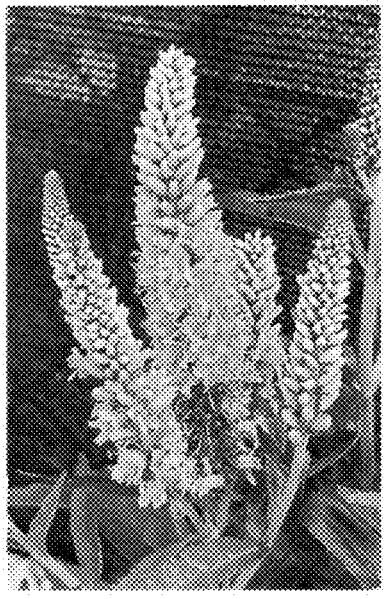
FIG. 2 illustrates a close-up view of inflorescences of 'Balskywink'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2022 under natural light conditions in Naperville, Ill.

The following descriptions and measurements describe approximately four-month old plants produced from cuttings from stock plants and grown in a polycarbonate-covered greenhouse under conditions comparable to those used in commercial practice. Approximately six weeks after sticking, rooted plants were transplanted three plants per one-gallon containers utilizing a soilless growth medium and grown for three weeks. Plants were then transferred to an outdoor nursery environment in West Chicago, Ill. and grown for approximately two months. Plants were given one pinch at approximately two weeks before transplant and another one week after transplant. Prior to transplant plants were grown in liners in a polycarbonate greenhouse in West Chicago, Ill. Greenhouse temperatures were maintained at approximately 70° F. to 75° F. (21.1° C. to 23.9° C.) during the day and approximately 60° F. to 65° F. (15.6° C. to 18.3° C.) during the night. Supplemental lighting was used. Measurements and numerical values represent averages of typical plants.

Botanical classification: *Veronica* hybrid 'Balskywink'.

Parentage:

*Female parent.*—Proprietary *Veronica spicata* breeding selection coded X14-6480-4, not patented.

*Male parent.*—First Love 'Allove', U.S. Plant Pat. No. 21,478.

Propagation:

*Type cutting.*—Terminal stem.

*Time to initiate roots.*—Approximately 7 to 10 days.

*Time to produce a rooted cutting.*—Approximately 35 to 42 days.

*Root description.*—Fibrous.

*Rooting habit.*—Freely branching.

Plant description:

*Commercial crop time.*—Approximately 10 to 12 weeks from a rooted cutting to finish in a 15 cm pot.

*Growth habit and general appearance.*—Herbaceous perennial, moderately vigorous, compact, upright.

*Hardiness.*—USDA Zone 4b (−25° F. to −20° F./−31.7° C. to −28.9° C.).

*Size.*—Height from soil level to top of plant plane: Approximately 33.0 cm. Width: Approximately 38.0 cm.

*Branching habit.*—Freely branching, pinching enhances basal branching. Quantity of main branches per plant: Approximately 7.

*Branch.*—Strength: Strong. Branch height to bottom of inflorescence: Approximately 20.0 cm. Diameter: Approximately 4.0 mm. Length of central internode: Approximately 2.0 cm. Texture: Densely pubescent with appressed and curled hairs. Color of young stems: 146B. Color of mature stems: 146B, becoming woody 200D with age.

Foliage description:

*General description.*—Quantity of leaves per main branch: Approximately 16. Fragrance: None detected. Form: Simple. Arrangement: Opposite, decussate.

*Leaves.*—Aspect: Perpendicular to stem. Shape: Narrowly ovate. Margin: Serrate. Apex: Broadly acute. Base: Rounded. Venation pattern: Pinnate. Length of mature leaf: Approximately 8.0 cm. Width of mature leaf: Approximately 2.5 cm. Texture of upper surface: Sparsely pubescent. Texture of lower surface: Sparsely pubescent only on venation. Color of upper surface of young and mature foliage: Closest to NN137A. Color of lower surface of young and mature foliage: Closest to 137C. Venation of upper and lower surface: 147C.

*Petioles.*—Length: Approximately 1.5 cm. Width: Approximately 3.0 mm. Texture: Sparsely pubescent. Color: 147C.

Flowering description:

*Flowering habit.*—'Balskywink' is a long-day facultative, freely flowering under outdoor growing conditions blooming from late spring through summer.

*Lastingness of individual flower on the plant.*—Approximately 7 days.

Inflorescence description:

*General description.*—Type: Terminal raceme, self-cleaning. Fragrance: None detected. Height: Approximately 8.0 cm to 10.0 cm. Width: Approximately 1.5 cm to 2.0 cm. Quantity per plant: Approximately 5.

*Peduncle.*—Strength: Strong. Aspect: Erect and acute angle to stem. Length: Approximately 1.0 cm to 5.0 cm. Diameter: Approximately 2.0 mm to 3.0 mm. Texture: Densely pubescent with appressed and curled hairs. Color: 146B.

Flower description:

*General description.*—Type: Single, salverform. Aspect: Outward. Quantity of fully open flowers per inflorescence: Approximately 90.

*Bud.*—Rate of opening: Generally takes 3 to 4 days for bud to progress from first color to fully open flower.

*Bud just before opening.*—Shape: Oblong. Length: Approximately 7.0 mm. Diameter: Approximately 2.0 mm. Texture: Glabrous. Color: N66D.

*Corolla.*—Height: Approximately 8.0 mm. Diameter: Approximately 9.0 mm.

*Petals.*—Quantity: 4. Appearance: Dull. Shape: Elliptic. Margin: Entire, wavy. Apex: Broadly acute to rounded. Base: Fused into tube. Length: Approximately 4.0 mm to 5.0 mm. Width: Approximately 2.0 mm to 3.0 mm. Texture of upper and lower surfaces: Glabrous. Color of upper surface when first and fully open: Closest to but lighter than NN74D. Color of lower surface when first and fully open NN74D.

*Corolla tube.*—Length: Approximately 3.0 mm. Diameter at tube opening: Approximately 3.0 mm. Texture of inner surface: Densely pubescent. Color of pubescence: NN155D. Texture of outer surface: Glabrous. Color of inner and outer surfaces: Lighter than NN74D with NN155D at base.

*Calyx.*—Shape: Cupped. Depth: Approximately 3.0 mm. Diameter: Approximately 4.0 mm.

*Sepals.*—Quantity per flower: 4. Shape: Lanceolate, fused at base. Apex: Acute. Length: Two larger sepals approximately 3.0 mm and two smaller sepals approximately 2.0 mm. Width of all sepals: Approximately 1.0 mm. Texture of upper (inner) surface: Glabrous. Texture of lower (outer) surface: Sparsely pubescent. Color of upper and lower surfaces: 137A with 146D at base.

*Pedicel.*—Strength: Strong, flexible. Aspect: Approximately 45° angle from peduncle. Length: Approximately 2.0 mm. Diameter: Approximately 0.5 mm. Texture: Densely pubescent. Color: 146B.

*Reproductive organs.*—Androecium: Stamen quantity: 2 per flower. Stamen length: Approximately 8.0 mm. Filament color: 75C. Anther shape: Sagittate, dorsifixed. Anther length: Approximately 1.0 mm. Anther color: N81B. Pollen amount: Sparse. Pollen color: 2D. Gynoecium: Pistil quantity: 1 per flower. Pistil length: Approximately 8.0 mm. Stigma shape: Rounded. Stigma length: Less than 1.0 mm. Stigma color: 86A. Style length: Approximately 6.0 mm. Style color: N82B. Ovary length: Approximately 2.0 cm. Ovary color: 144A.

Seed and fruit production: Neither seed nor fruit production has been observed.

Disease and pest resistance: Resistance to pathogens and pests common to *Veronica* has not been observed.

What is claimed is:

1. A new and distinct cultivar of *Veronica* plant named 'Balskywink', substantially as herein illustrated and described.

* * * * *